United States Patent
Aitaru et al.

(10) Patent No.: US 10,401,346 B2
(45) Date of Patent: Sep. 3, 2019

(54) MOBILE SICKLE CELL DIAGNOSTIC TOOL

(71) Applicants: Rachel Olema Aitaru, Kampala (UG); Bonita Beatrice Nanziri, Kampala (UG)

(72) Inventors: Rachel Olema Aitaru, Kampala (UG); Bonita Beatrice Nanziri, Kampala (UG)

( * ) Notice: Subject to any disclaimer, the term of this patent is extended or adjusted under 35 U.S.C. 154(b) by 0 days.

(21) Appl. No.: 15/355,919

(22) Filed: Nov. 18, 2016

(65) Prior Publication Data
US 2018/0143179 A1    May 24, 2018

(30) Foreign Application Priority Data
Sep. 16, 2016    (UG) .............................. P/2016/000007

(51) Int. Cl.
| | |
|---|---|
| *G01N 33/49* | (2006.01) |
| *G01N 21/01* | (2006.01) |
| *G01N 15/14* | (2006.01) |
| *G01N 33/487* | (2006.01) |
| *A61B 5/00* | (2006.01) |
| *G06K 9/00* | (2006.01) |
| *G01N 15/00* | (2006.01) |
| *G01N 15/10* | (2006.01) |

(52) U.S. Cl.
CPC .......... *G01N 33/49* (2013.01); *A61B 5/0082* (2013.01); *G01N 15/1468* (2013.01); *G01N 15/1475* (2013.01); *G01N 21/01* (2013.01); *G01N 33/48785* (2013.01); *G06K 9/00127* (2013.01); *G01N 2015/0073* (2013.01); *G01N 2015/1006* (2013.01); *G01N 2201/0221* (2013.01); *G06T 2207/10056* (2013.01); *G06T 2207/20024* (2013.01)

(58) Field of Classification Search
CPC ....... G01N 33/49; G01N 21/01; A61B 5/0082
USPC .......................................................... 356/39
See application file for complete search history.

(56) References Cited

U.S. PATENT DOCUMENTS

| | | | | |
|---|---|---|---|---|
| 4,175,860 A | * | 11/1979 | Bacus ................ | G06K 9/00127 356/39 |
| 6,778,698 B1 | * | 8/2004 | Prakash ................. | G06K 9/342 382/164 |

(Continued)

FOREIGN PATENT DOCUMENTS

WO    2016/094521    6/2016

OTHER PUBLICATIONS

Dreslaeur et. al., "Mobile Phone Based Clinical Microscopy for Global Health Applications" Jul. 22, 2009; 8 pgs.

(Continued)

*Primary Examiner* — Roy M Punnoose

(57) ABSTRACT

Implementing a mobile device configured to detect sickle cell traits in a blood sample. The device comprises a mobile device with a camera operatively coupled to a microscope lens. An image converter configured to receive an image form the camera and to perform a noise reduction procedure. The noise reduction procedure manipulates the image to a monochrome image and applies a Gaussian filter. A contour detector detects the contours of the image. An image analysis tool is configured to analyze the contours to identify discrete blood cells and clustered blood cells. The user is then notified if sickle cell traits are present based at least on the shape of the discrete blood cells.

17 Claims, 7 Drawing Sheets

(56) References Cited

U.S. PATENT DOCUMENTS

| | | |
|---|---|---|
| 8,916,390 B2 | 12/2014 | Ozcan et al. |
| 9,696,535 B2 * | 7/2017 | Prakash ............. G02B 21/0076 |
| 2008/0318194 A1 * | 12/2008 | Atchison ................ G09B 23/30 |
| | | 434/267 |
| 2013/0203043 A1 | 8/2013 | Ozcan et al. |
| 2015/0247565 A1 | 9/2015 | Irish et al. |
| 2017/0146784 A1 * | 5/2017 | Schmidt ............... G02B 21/361 |
| 2017/0234874 A1 * | 8/2017 | Adams ............. G01N 33/56966 |
| | | 435/7.21 |

OTHER PUBLICATIONS

Tuijn et. al., "Data and Image Transfer Using Mobile Phones to Strengthen Microscopy-Based Diagnostic Services in Low and Middle income Country Laboratories" Dec. 14, 2011.

Examination Report issued in UG/P/2016/00007, dated Jun. 19, 2017, 2 pgs.

\* cited by examiner

MOBILE SICKLE CELL DIAGNOSTIC TOOL

BACKGROUND

Background and Relevant Art

Sickle cell disease (SCD) describes a group of inherited red blood cell disorders, wherein individuals affected with SCD have sickle hemoglobin present in their red blood cells. In severe cases, if both parents are sickle-cell carriers, the patient may have sickle cell disease.

In many parts of the world, determining whether an individual has sickle cell disorder can take several weeks to months to determine and can be expensive because of testing procedures. The process requires a medical professional to take a blood sample and properly prepare the sample. Then a specialized medical professional analyzes the blood sample. The analysis often requires expensive, specialized equipment in a laboratory setting. In communities with a strong medical system, this process may take a few days to a few weeks. In communities where there is less access to medical resources and/or medical professionals, the diagnosis can take weeks or months. In poor communities, even if the medical resources and medical professionals are available, the cost of such tests may be prohibitive.

This delay in diagnosis dramatically affects patient outcomes. In high-income countries like the United States, the life expectancy of a person with SCD is now about 40-60 years. In 1973, the average lifespan of a person with SCD in the United States was only 14 years. Advances in the diagnosis and care of SCD have made this improvement possible. In low income countries, survival is much shorter. For example, in Uganda, 30,000 babies are born annually with sickle cell and 80% of these children die before the age of five.

Given the dramatic difference in outcomes, improved devices are required for early detection of SCD for patients located in sub-Saharan Africa. In particular, electrical infrastructure and internet infrastructure challenges require a portable solution that can be deployed easily.

BRIEF SUMMARY

One embodiment illustrated herein includes a mobile device configured to detect sickle cell traits in a blood sample. The device comprises a mobile device with a camera operatively coupled to a microscope lens. An image converter configured to receive an image form the camera and to perform a noise reduction procedure. The noise reduction procedure converts the image to a monochrome image and applies a Gaussian filter. A contour detector detects the contours of the image. An image analysis tool is configured to analyze the contours to identify discrete blood cells and clustered blood cells. The user is then notified if sickle cell traits are present based at least on the shape of the discrete blood cells.

BRIEF DESCRIPTION OF THE DRAWINGS

To describe the manner in which the above-recited and other advantages and features can be obtained, a more particular description of the subject matter briefly described above will be rendered by reference to specific embodiments which are illustrated in the appended drawings. Understanding that these drawings depict only typical embodiments and are not therefore to be considered to be limiting in scope, embodiments will be described and explained with additional specificity and detail through the use of the accompanying drawings in which.

DETAILED DESCRIPTION

Methods and apparatus are disclosed herein that provide a mobile sickle cell diagnostic tool. The mobile sickle cell diagnostic tool may comprise a handheld computing device, lighting source and lens. The mobile sickle cell diagnostic tool may enable a faster and more cost-effective way to diagnose people with sickle cell disease (SCD).

The mobile sickle cell diagnostic tool is configured to provide a light source to illuminate a prepared blood slide. The mobile sickle cell diagnostic tool can then capture the image, process the image, analyze the processed image, and then detect the presence of sickle hemoglobin in the patient's blood. Based on the results of the detection process, the mobile sickle cell diagnostic tool can generate appropriate reports, notifications, and alerts for the user.

In an example embodiment, the mobile sickle cell diagnostic tool, may comprise a mobile computer with an integrated camera and an attachable microscope lens to capture a magnified image of a blood sample. The mobile sickle cell diagnostic tool may be configured to manipulate the image by enhancing characteristics of the image in order to identify a predetermined set of SCD markers. In an embodiment, the image capture, manipulation, and identification may occur on the mobile sickle cell diagnostic tool. In an alternative embodiment, the identification of the SCD may occur on a server accessible via the internet and the results shared back to the user of the mobile device.

Figure 1:
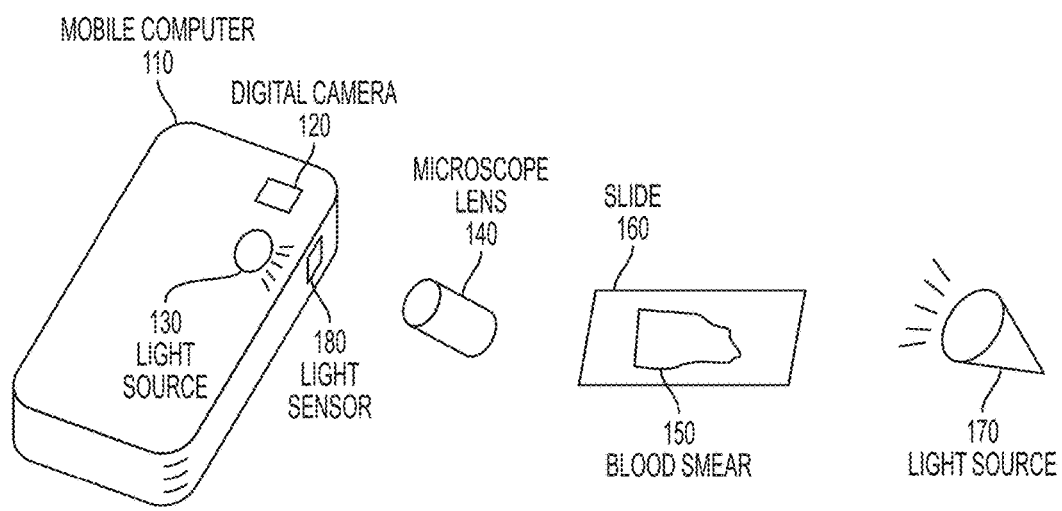
FIG. 1 illustrates a mobile sickle cell diagnostic tool.

FIG. 1 illustrates an example of a mobile sickle cell diagnostic tool 100 configured to capture an image of a blood smear 150 on a slide 160. The mobile sickle cell diagnostic tool 100 shown in FIG. 1 includes a mobile computer 110. While FIG. 1 shows the mobile computer 110 as a smartphone, this is an example embodiment. Alternatively, the mobile computer 110 may be a tablet computer, or other device with image capture, image analysis and communication capabilities.

FIG. 1 further shows a blood sample on a slide 160. The slide 160 is a transparent surface that holds objects that are viewed under the microscope lens 140. In preparing the blood sample, the blood sample may be prepared as a blood smear 150 where a monolayer is created so that the cells are spaced far enough apart to be counted and differentiated. The blood smear 150 may be further prepared by applying a stain to the blood. Different types of stains may include Romanowsky, Wright's, or Giemsa stain. The preparation of the blood sample or blood stain may additionally include steps and additive elements that trigger the red blood cells to take the shape of sickle cells.

The mobile sickle cell diagnostic tool 100 further comprises a digital camera 120 to capture the image. For example, the digital camera 120 may comprise a sensor and digital image processing. The sensor may comprise, e.g., a charge-coupled device (CCD), a complementary metal-oxide-semiconductor (CMOS) sensor, back side illuminated CMOS sensor, a three-dimensional camera, and/or a combination thereof. The digital camera 120 converts an analog input image to a digital image. The mobile sickle cell diagnostic tool 100 further comprises an adjustable light source 130 that may illuminate the blood smear 150 to enhance the image for processing. For example, the light source 130 can be an LED, xenon tube, incandescent bulb, etc. The mobile sick cell diagnostic tool 100 may be configured to adjust the wavelength of the light source (e.g. color), the intensity and or/direction.

The mobile sickle cell diagnostic tool 100 further includes a microscope lens 140 that provides an optical and/or digital magnification of the subject to which the microscope lens 140 is directed. In the embodiment, the image is magnified so that discrete objects can be identified in the blood. Additionally, or alternatively, the magnification may, in part, be provided by the digital camera 120. The mobile sickle cell diagnostic tool 100 may be configured to apply image magnification to all or a portion of the image during the image capture stage and during post processing. In one scenario, the mobile sickle diagnostic tool 100 may receive, via a feedback loop, an indication that a particular section of an image cannot be analyzed to a predetermined level of accuracy, accordingly the mobile sickle diagnostic tool 100 may magnify only that portion of the image for additional processing. The magnification may be 400× or greater. In some embodiments, the range may be between 400× to 1000×. The microscope lens 140 may be operatively attached to the mobile computer 110.

FIG. 1 further shows one or more external tight sources 170 that may illuminate the blood smear 150. In some embodiments, the external light source 170 may illuminate the side opposite the microscope lens 140 thereby producing a backlight to the slide. This backlight may be made at any angle relative to the slide in order to provide the backlight. In an alternative embodiment, the external light source 170 may be on the same side as the microscope lens 140.

The mobile sickle cell diagnostic tool 100 may further comprise one or more light sensors 180. The light sensor 180 can detect ambient light, and/or light from the light source 130, and/or light from the external light source 170. The information from the light sensor 180 may be used by the mobile compute 110 to adjust the light source 130 and/or external light source 170 within a predetermined light range and/or used to provide data for digital image processing and analysis. For example, the light sensor could use a photodiode to determine the brightness, color space, tint, hue of the blood smear 150. Based on the determination of the brightness, the light sensor 180 may automatically adjust the wavelength, intensity, or other characteristics of the light source 130

Figure 2:
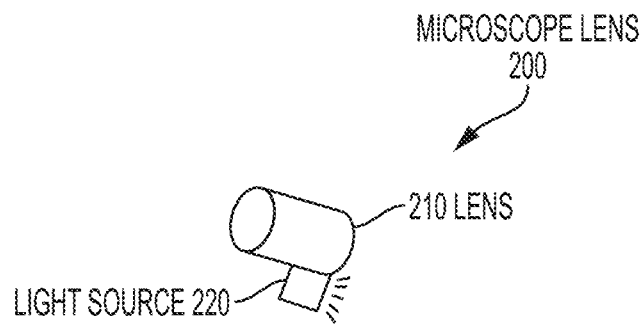
FIG. 2 illustrates details of an embodiment of a microscope lens.

FIG. 2 illustrates an embodiment of the microscope lens 200 where the lens 210 and a light source 220 are operatively coupled. The light source 220 is attached to the lens 210 so that the light is directed away from the lens.

Figure 3:
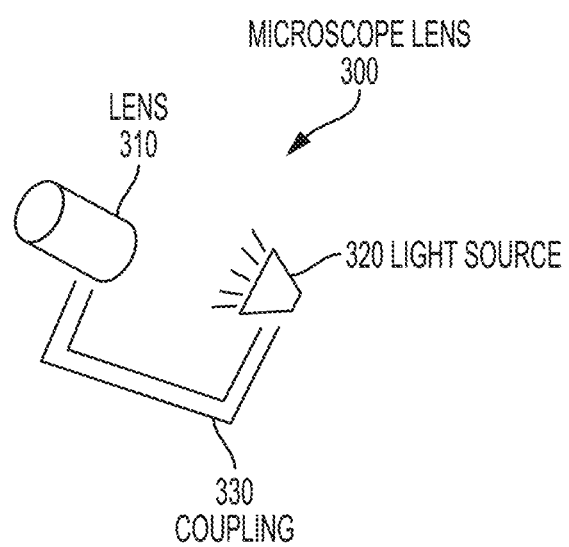
FIG. 3 illustrates details of an alternative embodiment of a microscope lens.

FIG. 3 illustrated an alternative embodiment to a microscope lens. In this embodiment, the microscope lens 300 comprises a lens 310 and a light source 320. The light source is operationally coupled by a coupler 330 so that the light is directed towards the lens.

Figure 4:
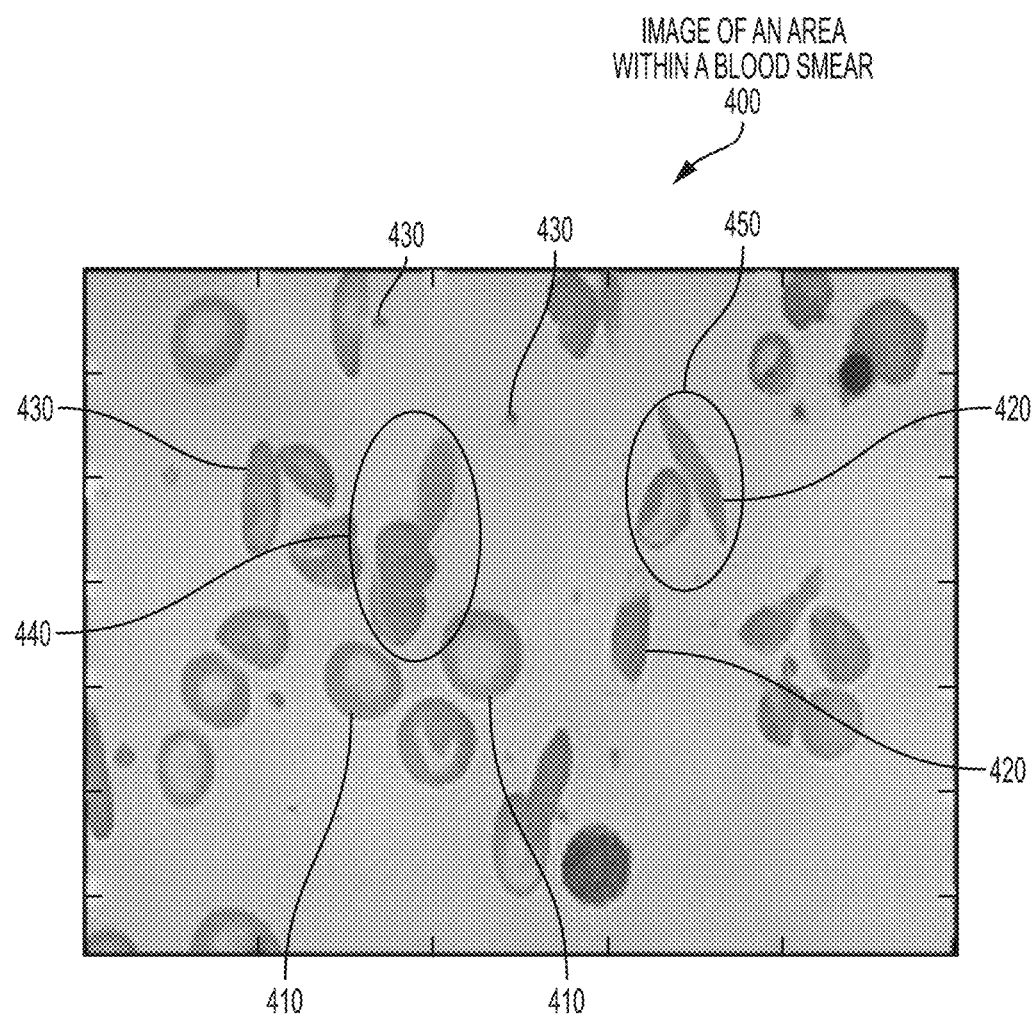
FIG. 4 illustrates the details of an image of an area within a blood sample.

FIG. 4 illustrates an example of an image of an area within a blood smear 400. This image comprises healthy, or normal red blood cells 410, sickle cells 420, and non-red blood cell objects 430. Objects may stack on each other 440 or be touching with minimal overlap 450.

Figure 5:
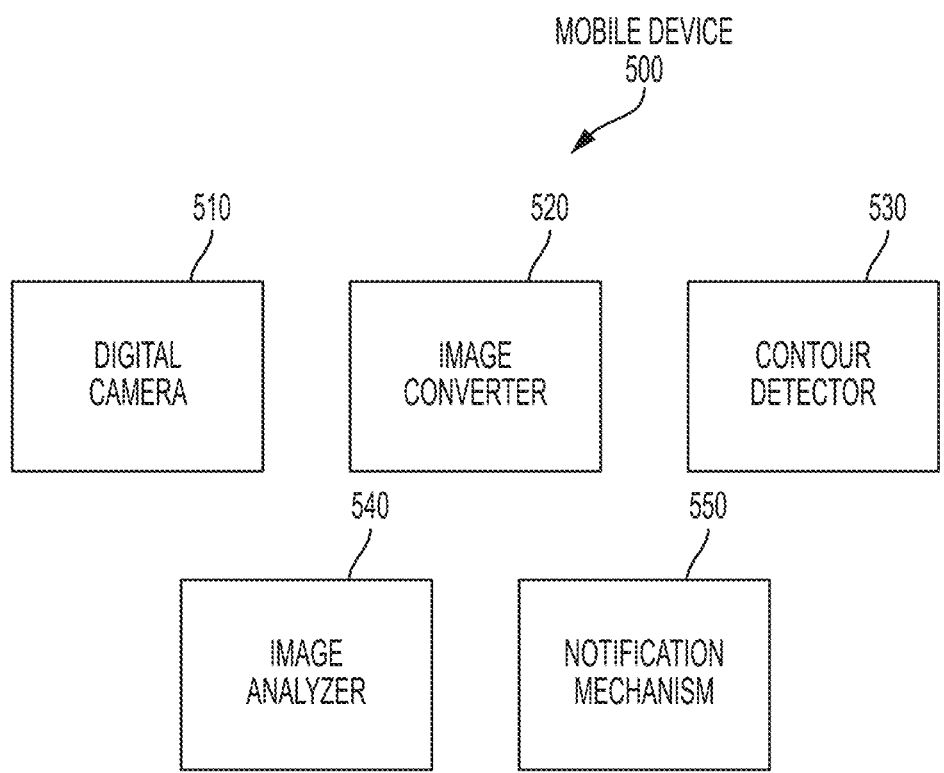
FIG. 5 illustrates the components of a computing device to detect sickle cells.

FIG. 5 shows the components of the sickle cell detector configured according to the present invention. The mobile device 500 includes a digital camera 510, an image converter 520, a contour detector 530, an image analyzer 540, and a notification mechanism 550.

The digital camera 510 captures a digital image of the blood smear 150. In the embodiment, the image is magnified so that discrete objects can be identified in the blood.

The image converter 520 modifies the original image by applying one or more noise reduction techniques and/or conversions. The noise reduction filters and/or conversions are applied to emphasize the prominent objects in the image which makes a red blood cell (RBC) and similarly sized objects more detectable by emphasizing the color contrasts in their shape. This process also reduces, or blurs, the shape of objects substantially smaller than an RBC in order to emphasize objects substantially smaller than an RBC. In one embodiment, a monochromatic filter may be applied, Additionally, or alternatively, a blurring filter can be applied to the image. As an example, a Gaussian Blur can be applied to blur the image. Additionally, or alternatively, the image can be cropped and/or magnified to enlarge objects in the image.

The contour detector 530 can be applied to determine the edges of objects in the image. Additionally, the contour detector 530 may determine significant shape changes in objects. Alternatively, the contour detector 530 may be included as part of the image analyzer 540 component.

The image analyzer 540 analyzes the shapes of the one or more objects in the image to determine discrete objects, specifically identifying normal RBC and abnormal RBC. Sickle cells are identified by their elliptical shape that may be identified by determining a height that is substantially greater than its width. Normal, or healthy, RBCS are substantially circular and in some case may include an inner and outer substantially circular edge 410 (in FIG. 4). The object shapes are in part determined by using five or more points along a continuous contour. An alternative embodiment may further analyze the blood cell shapes by applying different ratios and/or calculations based on patient attributes comprising age and/or ethnicity.

Additional objects in the image may also be identified. The mobile sickle cell diagnostic tool to may include a predetermined minimum RBC threshold value and a predetermined maximum RBC threshold value. The mobile sickle cell diagnostic tool may be configured to compare each identified object with the predetermined minimum RBC threshold value and maximum RBC threshold value. Based on this comparison, objects smaller than the predetermined minimum RBC threshold value may be ignored by the image analyzer. Objects larger than the maximum predetermined RBC threshold value may be further analyzed and/or ignored by the image analyzer 540. For example, two or more blood cells can be stacked on top of each other 440. In such a case, the image analyzer 540 may identify the object on top and provide further analysis on that object. As an alternative example, two or more RBC may be touching (as illustrated in 450) and the image analyzer 540 may identify the two or more objects and treat them as discrete objects.

The notification mechanism 550 is configured to generate a notification based on the results of the image analyzer 540. In an embodiment, the user of the mobile device is notified of whether sickle cell traits are present or not. In an alternate embodiment, a health care provider could be notified by accessing a web server and/or a health care system.

In an alternative embodiment, the image converter 520, the contour detector 530, and/or the image analyzer 540 could be executed on one or more computers other than that used to capture the image. For example, the image may be captured by the digital camera 120 and that image may be shared with a server. The server may then manipulate the image, detect the contours, and/or analyze the image. In an alternative embodiment, each of the steps conducted on a server may be executed on different servers.

In another alternative embodiment, two or more images can be compared to determine sickle cells. In one example, the original digital image and the manipulated image may both be analyzed and characteristics of each can identify objects in the blood sample. For example, in the manipulated image, multiple blood cells being stacked upon each other may be difficult to detect, but in the non-manipulate image, the stacking might be more clear. The image analyzer 540 may use both images to identify an object. In another example, two or more images that apply different manipulation techniques may be compared to identify objects in the blood sample.

In an alternative embodiment, the image analyzer 540 may manage the rate of false positive and false negative determinations. A false positive occurs when the image analyzer determines that sickle cells are present when in fact they are not present. A false negative occurs when the image analyzer does not detect sickle cells even though they are present in the image. As an example a user may configure the image analyzer 540 to reduce the likelihood of a false positives to a specified range by setting a range enabled by the mobile sickle cell diagnostic tool. As another example, a user may configure the image analyzer to reduce the likelihood of false negatives and/or increase the likelihood of false positives. This latter example may be used if the mobile sickle cell diagnostic tool is used as an initial screening for sickle cell disorder and subsequent tests would be administered if the patient is likely to have sickle cells disease. As another example, the tolerances for the false positive or false negative may be within a predefined range and the user does not need to configure these settings.

Figure 6:
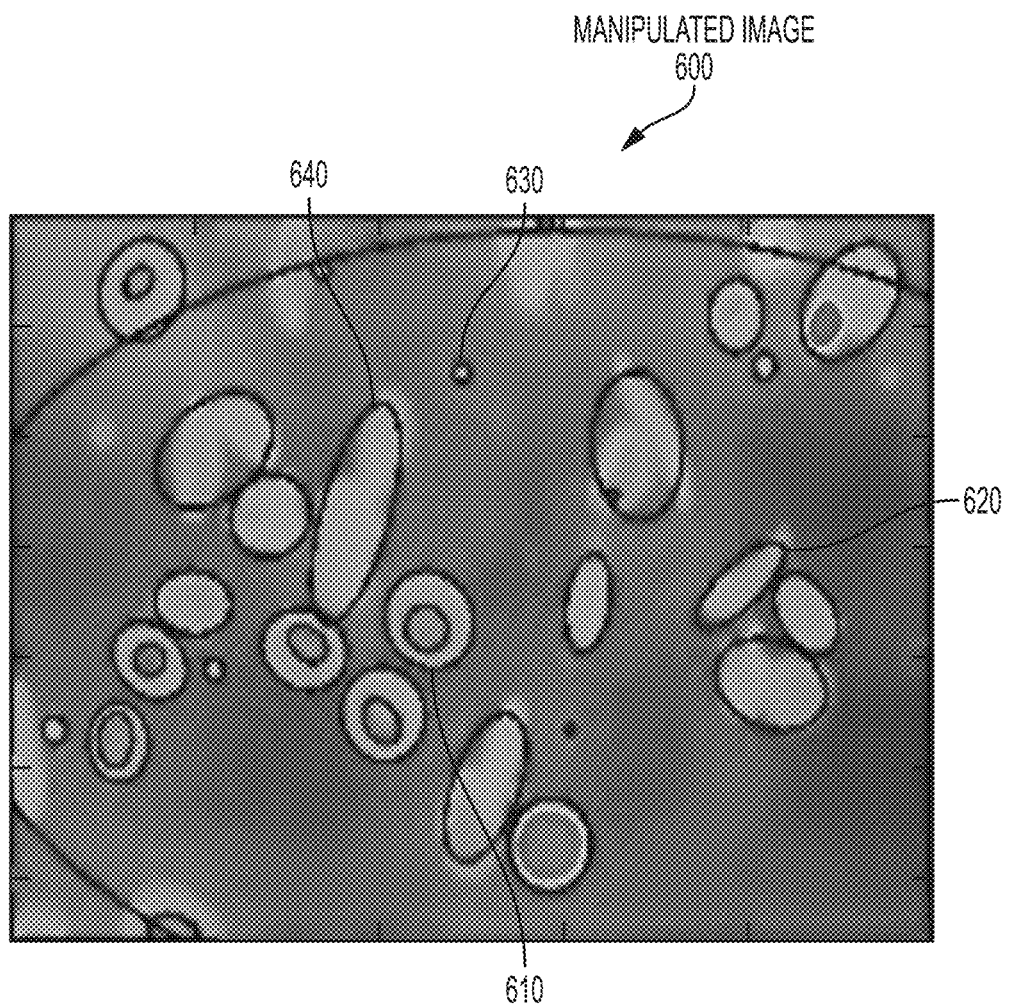
FIG. 6 illustrates details of a manipulated image of an area within a blood sample.

FIG. 6 illustrates a manipulated image 600. The image comprises a health, or normal, red blood cell 610, sickle cells 620, non-red blood cell objects 630, and red blood cells stacked on each other 640.

Figure 7:
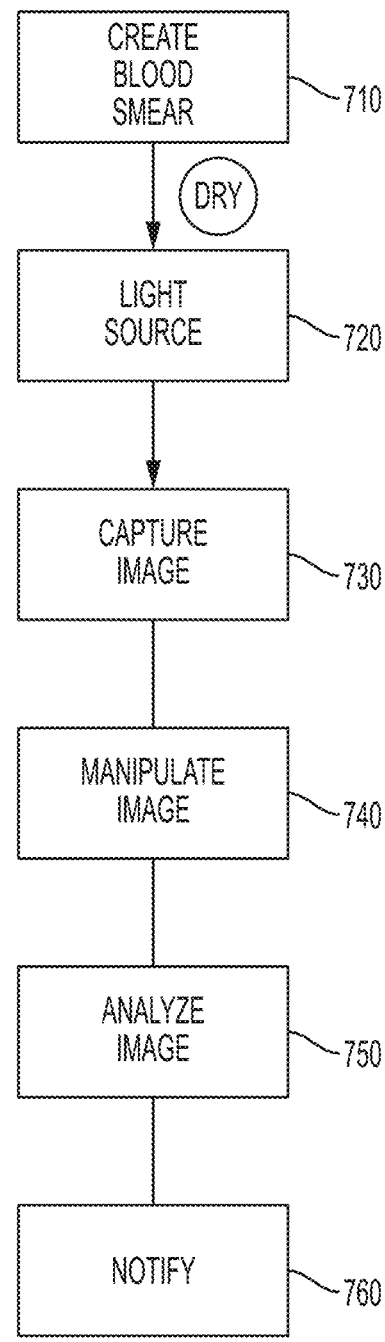
FIG. 7 illustrates a method for detecting sickle cell on a mobile device.

FIG. 7 is a flowchart for detecting sickle-blood-cell traits according to an embodiment herein. A slide is prepared and a blood sample is applied to the slide to create a blood smear (act of 710). The blood smear is viewed through the digital camera 120 and microscope lens 140 of the mobile sickle cell diagnostic tool 100. One or more light sources are used to illuminate the blood smear (act of 720). A light source may illuminate the front side of the smear relative to the microscopic lens. Alternatively, or additionally, the back side of the smear relative to the microscopic lens may be illuminated. As an alternative embodiment, the light source could be ambient light. An image of the blood smear is captured through the digital camera (act of 730). Image processing is applied to manipulate the image (act of 740). The manipulated image is analyzed to determine objects in the blood smear (act of 750). The results of the analysis are communicated to the user and/or a health care professional (act of 760).

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Figure 8:
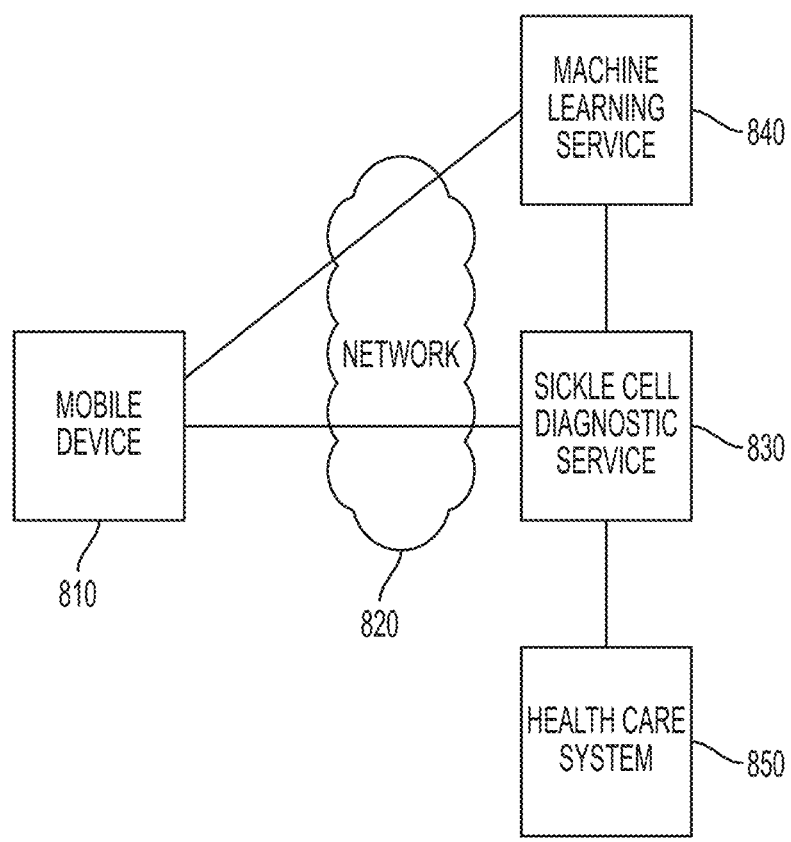
FIG. 8 illustrates details of an alternative embodiment where resources available external to the Mobile Device are used in coordination with the Mobile Device.

FIG. 8 illustrates an alternative embodiment of the mobile sickle cell diagnostic tool 100. The sickle cell diagnostic tool 100 may be configured to communicate all or a portion of the image data to external computers for processing. In this scenario, the mobile sickle cell diagnostic tool may be configured to encrypt all or a portion of the image data to the external computer, depending on the computing capacity of the mobile sickle diagnostic tool 100, the image data may be processed or unprocessed data. The external computers may be configured to perform processing and transmit a processed image or the results of the analysis back to the mobile sickle cell diagnostic tool. The image data may be transmitted from the mobile device 810 to a sickle cell diagnostic service 830 associated with the external computer over a wired or wireless network 820. In an alternative embodiment, the image from mobile device 810 may be transmitted to an alternate computer that can later transmit the image to the sickle cell diagnostic service 830. The sickle cell diagnostic service 830 may conduct some or all of the steps of converting the image, analyzing the image, and notifying the user.

In addition to, or alternatively the system of FIG. 8, the system may additionally notify the results of the analysis to a health care system 850. The health care system 850 may be a notification system for health care professionals. The health care system 850 may by a medical record management system or other software package used by healthcare professionals.

In an alternative embodiment, Machine Learning techniques from a machine learning service 840 may be applied to the image analysis component. The image recognition techniques may be applied to normal and abnormal RBCs to more accurately and/or more quickly identify sickle cells and other objects in the image. The Machine Learning technique may alternatively be applied to the image converter and/or contour detector. As an example, Machine Learning may determine new markers and/or metrics to differentiate sickle cells from non-sickle cells. As an alternative example, machine learning may determine new markers and/or metrics to differentiate and/or identify normal RBCs, abnormal RBCs, and/or other objects in the blood smear.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry or desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be priced in network computing environments with many types of computer system configurations including, personal computers, desktop computers, laptop computers, message processors, hand-held devices, multi-processor systems, microprocessor-based or programmable consumer electronics, network PCs, minicomputers, mainframe computers, mobile telephones, PDAs pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage device.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A mobile device for identifying sickle cells in an image of a blood smear comprising:
   a microscope lens operatively coupled to a camera;
   an image converter configured to receive an image from the camera and to perform a noise reduction procedure to generate a converted image, wherein the noise reduction procedure comprises:
      converting a color base of the image to monochrome;
      applying a Gaussian filter;
   a contour detector to detect contours in the converted image;
   an image analyzer configured to analyze the contours to identify discrete blood cells and clustered blood cells and to identify the shapes of the discrete blood cells by identifying at least five points along a continuous contour; and
   a notification mechanism configured to notify a user that sickle cell traits are present based on at least a shape of the discrete blood cells.

2. The mobile device of claim 1, further comprising a light source configured to provide light in a predetermined light range.

3. The mobile device of claim 1, wherein the image analyzer is configured to identify substantially round particles as normal red blood cells.

4. The mobile device of claim 1, wherein the image analyzer is configured to identify substantially elliptical blood cells as sickle cells.

5. The mobile device of claim 4, wherein the identification of sickle cells is based in part on patient attributes comprising age.

6. The mobile device of claim 1, wherein clustered blood cells are identified by comparing an original image and the converted image to identify sickle cells.

7. A system for detecting sickle cells in an image of a blood smear comprising:
   an image converter configured to perform a noise reduction procedure on a magnified image of a blood smear, wherein the noise reduction procedure comprises:
      converting a color base of the image to monochrome;
      applying a Gaussian filter,
   a contour detector to detect contours in the converted image;
   an image analyzer is configured to analyze the contours to identify a shape of an object in the blood smear by identifying at least five points along a continuous contour, and
   a notification mechanism configured to notify a user that sickle cell traits are present based on at least the object's shape.

8. The system of claim 7, wherein the image analyzer is configured to identify substantially round particles as normal red blood cells.

9. The system of claim 7, wherein the image analyzer is configured to identify substantially elliptical blood cells as sickle cells.

10. The system of claim 9, wherein the identification of sickle cell is based in part on patient attributes comprising age.

11. The system of claim 7, wherein clustered blood cells are identified by comparing an original image and the converted image to identify sickle cells.

12. The system of claim 7, wherein the image analyzer is configured to use machine learning to identify objects in the blood smear.

13. A method for detecting sickle cells from a blood smear image, the method comprising:
 converting a blood smear image to a noise reduced blood smear image by applying a noise reduction procedure comprising:
  converting a color base of the blood smear image to monochrome; and
  applying a Gaussian filter;
 determining the contours of the objects in the noise reduced blood smear image;
 analyzing the objects of the noise reduced blood smear image to identify discrete blood cells and clustered blood cells;
 determining the shapes of the discrete blood cells by identifying at least five points along a continuous contour of each object; and
 providing a notification event upon determining that sickle cell traits are present on at least a shape of the one or more identified discrete blood cells.

14. The method of claim 13, wherein analyzing the objects of the noise reduced blood smear image identifies substantially round objects as normal red blood cells.

15. The method of claim 13, wherein analyzing the objects of the noise reduced blood smear image identifies substantially elliptical blood cells as sickle cells.

16. The method of claim 13, wherein the identification of sickle cell is based in part on patient attributes comprising age.

17. The method of claim 13, wherein identifying clustered blood cells by comparing an original image and the converted image to identify sickle cells.

* * * * *